United States Patent
Betancourt

(10) Patent No.: US 10,273,449 B2
(45) Date of Patent: *Apr. 30, 2019

(54) INDUCTION MEDIUM AND METHODS FOR STEM CELL CULTURE AND THERAPY

(71) Applicant: SanBio, Inc., Mountain View, CA (US)

(72) Inventor: Aline Betancourt, La Jolla, CA (US)

(73) Assignee: SanBio, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/072,971

(22) Filed: Mar. 17, 2016

(65) Prior Publication Data

US 2016/0201036 A1    Jul. 14, 2016

Related U.S. Application Data

(60) Division of application No. 14/720,603, filed on May 22, 2015, now Pat. No. 9,321,994, which is a continuation of application No. 14/504,399, filed on Oct. 1, 2014, now abandoned.

(51) Int. Cl.
    *C12N 5/00*      (2006.01)
    *C12N 5/0775*    (2010.01)
    *A61K 35/12*     (2015.01)
    *A61K 35/28*     (2015.01)

(52) U.S. Cl.
    CPC ............ *C12N 5/0043* (2013.01); *A61K 35/28* (2013.01); *C12N 5/0662* (2013.01); *C12N 5/0663* (2013.01); *C12N 5/0668* (2013.01); *A61K 2035/124* (2013.01); *C12N 2500/02* (2013.01); *C12N 2500/92* (2013.01); *C12N 2501/00* (2013.01); *C12N 2501/052* (2013.01); *C12N 2501/14* (2013.01); *C12N 2501/22* (2013.01); *C12N 2501/2304* (2013.01); *C12N 2501/2313* (2013.01); *C12N 2501/24* (2013.01); *C12N 2501/25* (2013.01); *C12N 2501/58* (2013.01); *C12N 2501/599* (2013.01); *C12N 2501/90* (2013.01); *C12N 2501/999* (2013.01)

(58) Field of Classification Search
    CPC .. C12N 5/0043; C12N 5/0668; C12N 5/0663; C12N 5/0662; C12N 2501/599; C12N 2501/052; C12N 2501/2313; C12N 2501/14; C12N 2501/90; C12N 2501/2304; C12N 2501/999; C12N 2501/58; C12N 2501/24; C12N 2501/25; C12N 2501/22; C12N 2500/92; C12N 2501/00; C12N 2500/92; A61K 35/28; A61K 2035/124

See application file for complete search history.

(56) References Cited

U.S. PATENT DOCUMENTS

| | | |
|---|---|---|
| 2005/0265980 A1 | 12/2005 | Chen et al. |
| 2010/0008992 A1 | 1/2010 | Ichim |
| 2011/0044958 A1 | 2/2011 | Bartholomewq et al. |
| 2014/0017787 A1 | 1/2014 | Betancourt |
| 2014/0140968 A1 | 5/2014 | Kadouri et al. |
| 2014/0256043 A1 | 9/2014 | Kume et al. |
| 2015/0017132 A1 | 1/2015 | Aggarwal et al. |

FOREIGN PATENT DOCUMENTS

| | | |
|---|---|---|
| EP | 1727892 B1 | 5/2012 |
| WO | WO-2009114860 | 9/2009 |
| WO | WO-2011068792 A2 | 6/2011 |
| WO | WO-2012051210 A2 | 4/2012 |
| WO | WO-2017173150 A1 | 10/2017 |

OTHER PUBLICATIONS

Carrade et al. Comparative Analysis of the Immunomodulatory Properties of Equine Adult-Derived Mesenchymal Stem Cells. Cell Medicine, vol. 4, pp. 1-11, 2012 (Year: 2012).*
Aggarwal et al. Human mesenchymal stem cells modulate allogeneic immune cell responses. Blood 105(4):1815-1822 (2004).
Barcellos-De-Souza et al. Tumor microenvironment: Bone marrow-mesenchymal stem cells as key players. Biochimica et Biophysica Acta http://dx.doi.org/10.1016/j.bbcan.2013.10.004 (15 pgs.) (2013).
Bernardo et al. Mesenchymal stromal cells: Sensors and switchers of inflammation. Cell Stem Cell 13:392-402 (2013).
Betancourt et al. The role of mesenchymal stem cells in the tumor microenvironment, Chapter 12 in: Tumor microenvironment and myelomonocytic cells. Subhra K. Biswas (ed.) ISBN 978-953-51-0439-1 Available from: http://www.intechopen.com/books/tumor-microenvironment-and-myelomonocytic-cells/the-role-of-mesenchymal-stem-cells-in-the-tumor-microenvironment (pp. 255-287) (2012).
Betancourt. New cell-based therapy paradigm: Induction of bone marrow-derived multipotent mesenchymal stromal cells into pro-inflammatory MSC1 and anti-inflammatory MSC2 phenotypes Adv. Biochem. Eng. Biotechnol. DOI:10.1007/10_2012_141 (35 pgs.) (2012).
Bunnell et al. New concepts on the immune modulation mediated by mesenchymal stem cells. Stem Cell Res Ther 1(5):34 (2010).
Cassano et al. Mesenchymal stem cell therapy: Clinical progress and opportunities for advancement. Curr. Pathobiol Rep. 3:1-7 (2015).
Co-pending U.S. Appl. No. 14/504,399, filed Oct. 1, 2014.
Co-pending U.S. Appl. No. 14/720,603, filed May 22, 2015.
Co-pending U.S. Appl. No. 15/072,943, filed Mar. 17, 2016.
Ellestad et al. Early Life Exposure to Lipopolysaccharide Suppresses Experimental Autoimmune Encephalomyelitis by Promoting Tolerogenic Dendritic Cells and Regulatory T Cells. J Immunol 183:298-309 (2009).

(Continued)

Primary Examiner — Taeyoon Kim
(74) Attorney, Agent, or Firm — Levine Bagade Han LLP

(57) ABSTRACT

Novel MSC stem-cell culture and therapy methods and culture medium compositions for the purpose of inducing, activating, or priming discrete uniform cell phenotypes to selectively promote or suppress inflammation and immunity, yielding polarized, primed, activated, or induced cells used in cell-based therapy.

14 Claims, No Drawings

(56) References Cited

OTHER PUBLICATIONS

French et al. Enabling Consistency in Pluripotent Stem Cell-Derived Products for Research and Development and Clinical Application Through Material Standards. Stem Cells Translational Medicine 4: 1-7 (2015).
Gharibi et al. Immunomodulatory characteristics of mesenchymal stem cells and their role in the treatment of Multiple Sclerosis. Cellular Immunology 293:113-121 (2015).
Gieseke et al. Human multipotent mesenchymal stromal cells inhibit proliferation of PBMCs independently of IFNγR1 signaling and IDO expression. Blood 110(6):2197-2200 (2007).
Hinden et al. Ex-Vivo Induced Regulatory Human/Murine Mesenchymal Stem Cells as Immune Modulators. Stem Cells (16 pgs.) (2015).
Hoogduijn et al. Mesenchymal Stem Cells Induce an Inflammatory Response after Intravenous Infusion. Stem Cells and Development (34 pgs.) (2013) (doi:10.1089/scd.2013.0193).
Jeon et al. Cobalt chloride induces neuronal differentiation of human mesenchymal stem cells through upregulation of microRNA-124a. Biochem Biophys Res Commun. 444(4):581-587 (2014).
Kauffman et al. Whole genome analysis of the action of interferon-beta. Int J Clin Pharmacol Ther. 47(5):328-357 (2009).
Keating. Mesenchymal stromal cells: New directions. Cell Stem Cell 10:709-716 (2012).
Lalu et al. Safety of Cell Therapy with Mesenchymal Stromal Cells (SafeCell): A Systematic Review and Meta-Analysis of Clinical Trials. PLOS ONE 7(10):e47559 (2012).
Lee et al. Preactivation of Human MSCs with TNF-α Enhances Tumor-Suppressive Activity. Cell Stem Cell 11:1-11 (2012).
Li et al. Inflammatory environment induces gingival tissue-specific mesenchymal stem cells to differentiate towards a pro-fibrotic phenotype. (Running Title: Pro-fibrotic Differentiation of Inflammation Stem Cells). Society Fr des Micro DOI:10.1111/boc 201200064 (8 pgs.) (2013).
Liotta et al. TLR3 and TLR4 are expressed by human bone marrow-derived mesenchymal stem cells and can inhibit their T-cell modulatory activity by impairing notch signaling. Stem Cells 26(1):279-289 (2007).
Murphy et al. Mesenchymal stem cells: environmentally responsive therapeutics for regenerative medicine. Experimental & Molecular Medicine 45(e54):1-16 (2013).
New type of stem cell preparation could bring pain relief to diabetics PRWeb. (2 pgs.) (2012) // www.stemcellstm.com.
Nissen et al. Vascular Endothelial Growth Factor Mediates Angiogenic Activity during the Proliferative Phase of Wound Healing. Am J Path 152(6):1445-1552 (1998).
PCT/US2011/055831 International Preliminary Report on Patentability dated Apr. 16, 2013.
PCT/US2011/055831 International Search Report dated Jun. 13, 2012.
PCT/US2011/055831 Written Opinion dated Jun. 13, 2012.
PCT/US2015/52029 International Search Report and Written Opinion dated Feb. 10, 2016.
Prado-Lopez et al. The influence of hypoxia on the differentiation capacities and immunosuppressive properties of clonal mouse mesenchymal stromal cell lines. Immunology and Cell Biology DOI:10.1038/icb.2014.30 (12 pgs.) (2014).
Ryu et al. Tonsil-derived mesenchymal stromal cells produce CXCR2-binding chemokines and acquire follicular dendritic cell-like phenotypes under TLR3 stimulation. Cytokine 73:225-235 (2015).
Shin et al. Human Mesenchymal StemCell Grafts Enhance Normal and Impaired Wound Healing by Recruiting Existing Endogenous Tissue Stem/Progenitor Cells. Stem Cells Translational Medicine 2:000-000 (14 pgs.) (2013).
Tomchuck et al. Toll-like receptor 3 and suppressor of cytokine signaling proteins regulate CXCR4 and CXCR7 expression in bone marrow derived human multipotent stromal cells. PLOS ONE 7(6):e39592 (2012).
Tomchuck et al. Toll-like receptors on human mesenchymal stem cell drive their migration and immunomodulating responses. Stem Cells 26:99-107 (2008).
U.S. Appl. No. 14/720,603 Office Action dated Oct. 15, 2015.
U.S. Appl. No. 14/720,603 Office Action dated Sep. 3, 2015.
Van Den Akker et al. Mesenchymal stem cell therapy for cardiac inflammation: Immunomodulatory properties and the influence of toll-like receptors. Mediators of Inflammation, vol. 2013, Article ID 181020 http://dx.doi.org/10.1155/2013/181020 (13 pgs.) (2013).
Wang et al. CX43 change in LPS preconditioning against apoptosis of mesenchymal stem cells induced by hypoxia and serum deprivation is associated with ERK signaling pathway. Mol Cell Biochem (9 pgs.) (2013).
Wang et al. IFN-γ and TNF-α Synergistically Induce Mesenchymal Stem Cell Impairment and Tumorigenesis via NFkB Signaling. Stem Cells DOI: 10.1002/stem.1388 (22 pgs.) (2012).
Wang et al. Plasticity of mesenchymal stem cells in immunomodulation: pathological and therapeutic implications. Nature Immunology 15(11):1009 (2014).
Wang et al. Pre-treatment of human umbilical cord-derived mesenchymal stem cells with interleukin-6 abolishes their growth-promoting effect on gastric cancer cells, International Journal of Molecular Medicine DOI: 10.3892/ijmm.2014.2019 (9 pgs.) (2014).
Waterman et al. A New mesenchymal stem cell (MSC) paradigm: Polarization into a pro-inflammatory MSC1 or an immunosuppressive MSC2 phenotype. PLOS ONE 5(4):e10088 (2010).
Waterman et al. Anti-inflammatory mesenchymal stem cells(MSC2)attenuate symptoms of painful diabetic peripheral neuropathy. Stem Cells Translational Medicine 1:000-000 (10 pgs.) (2012).
Waterman et al. Mesenchymal stem cell 1(MSC1)-based therapy attenuates tumor growth whereasMSC2-treatment promotes tumor growth and metastasis. PLOS ONE 7(9):e45590 (2012).
Waterman et al. Treating chronic pain with mesenchymal stem cells: A therapeutic approach worthy of continued investigation. J. Stem Cell Res. Ther. S2:001 (5 pgs.) (2011) Doi.10:4172/2157-7633.S2-001.
Xinaris et al. A novel strategy to enhance Mesenchymal Stem Cell migration capacity and promote tissue repair in an injury specific fashion. CT-0390 Cell Transplantation (43 pgs.) (2012).
Yan et al. Priming of Toll-like receptor 4 pathway in mesenchymal stem cells increases expression of B cell activating factor. Biochemical and Biophysical Research Communications 448:212-217 (2014).
Zhang et al. Comparison of the therapeutic effects of human and mouse adipose-derived stem cells in a murine model of lipopolysaccharide-induced acute lung injury. Stem Cell Res. Ther. 4(1):13 pgs. (2013).
Zhang et al. Interleukin 6 mediates the therapeutic effects of adipose-derived stromal/stem cells in lipopolysaccharide-induced acute lung injury. Stem Cells (19 pgs.) (2014) doc.10.1002/stem.1632.
Zhao et al. MSCs derived from iPSCs with a modified protocol are tumor-tropic but have much less potential to promote tumors than bone marrow MSCs. PNAS 112(2):530-535 (2015).
Zwezdaryk et al. Erythropoietin, a hypoxia-regulated factor, elicits a pro-angiogenic program in human mesenchymal stem cells Exp. Hematol. 35:640-652 (2007).
PCT/US2015/52029 International Preliminary Report on Patentability dated Apr. 13, 2017.
Riazifar et al. Stem cell extracellular vesicles: Extended messages of regeneration. Annu Rev Pharmacol Toxicol 57:125-154 (2017).
PCT/US2017/025153 International Search Report and Written Opinion dated Aug. 25, 2017.
U.S. Appl. No. 15/072,943 Office Action dated Oct. 3, 2017.

\* cited by examiner

INDUCTION MEDIUM AND METHODS FOR STEM CELL CULTURE AND THERAPY

CROSS-REFERENCE

This application is a division of U.S. patent application Ser. No. 14/720,603, filed May 22, 2015; which is a continuation of U.S. patent application Ser. No. 14/504,399, filed Oct. 1, 2014, which applications are incorporated herein by reference in their entirety.

SUMMARY OF THE INVENTION

The invention provides novel stem-cell culture and therapy methods and culture medium compositions for the purpose of inducing, activating, or priming discrete uniform cell phenotypes to selectively promote or suppress inflammation and immunity, providing significant advantages over known culture media and methods, yielding primed, activated, or induced cells used in cell-based therapy. The invention can be used to provide more uniform and predictable ex-vivo expanded and induced, primed, or activated populations of MSC stem cells, which can be used for cell-based therapy. There is a long-felt need in the art for an improved method to provide a uniform and efficacious large number of stem cells required for cell-based therapy. An advantage of the various embodiments of the invention is that they can be used to induce, activate or prime cultures of multipotent stem cells into uniform and discrete phenotypes that behave in a predictable manner upon introduction into a patient.

UTILITY OF INVENTION

There is a need for improved therapeutic methods and improved cell-culture methods and media for inducing, activating, or priming uniform populations of MSCs—stem cells, mesenchymal stem cells, marrow stromal cells, multipotent stromal cells, multipotent stem cells—derived from various adult tissues. Clinical applications of MSCs require reproducible cell culture methods and cell expansion methods that provide adequate numbers of cells of suitable quality and consistent therapeutic benefits. Different culture media and methods have had varying degrees of success. There remains a need for further improvements to MSC culture media and methods that ensures expanded yields of primed, activated, or induced cells used in cell-based therapy having safe and consistently reproducible therapeutic effects.

The potency or therapeutic benefit of induced, activated, or primed MSC over un-induced conventional MSCs has been demonstrated in pre-clinical models of disease. Anti-inflammatory induced-MSC therapy alleviated pain and inflammation in models of painful diabetic peripheral neuropathy, rheumatoid arthritis, inflammatory bowel disease, and acute lung injury in a significantly improved manner over conventional MSC therapy. Additionally, anti-inflammatory induced-MSC therapy improved clinical scores, gait, and motor function in a pre-clinical model of multiple sclerosis (EAE) and Krabbe's disease. In a murine immune competent ovarian cancer model, the pro-immune anti-tumor induced-MSC cell-based immunotherapy led to attenuation of tumor growth and spread, whereas conventional MSC therapy promoted tumor growth and spread.

SCIENTIFIC BASIS OF THE INVENTION

The stimulation of specific Toll-like receptors (TLRs) affects the immune modulating responses of MSCs. Toll-like receptors recognize "danger" signals, and their activation leads to profound cellular and systemic responses that mobilize innate and adaptive host immune cells. The danger signals that trigger TLRs are released following most tissue pathologies. Since danger signals recruit immune cells to sites of injury, the Inventor reasoned that MSCs might be recruited in a similar way. The Inventor observed that MSCs express several TLRs (e.g., TLR3 and TLR4, known in the art), and that their migration, invasion, and secretion of immune modulating factors is drastically affected by specific TLR-agonist engagement. In particular, the Inventor observed diverse consequences to the MSCs following stimulation of TLR3 when compared to TLT4 by a low-level, short-term TLR-priming protocol. Based on these findings, the Inventor proposed a new paradigm for MSCs that took its cue from the monocyte literature. Specifically, that MSCs can be polarized (induced, activated, or primed) by downstream TLR signaling into two homogenously acting phenotypes classified as MSC1 and MSC2. TLR4-primed MSCs, or MSC1, mostly express pro-immunity inflammatory mediators, while TLR3-primed MSCs, or MSC2, mostly express anti-inflammatory or immunosuppressive ones. Additionally, the Inventor demonstrated that allogeneic (non-self) co-cultures of TLR-primed MSCs with peripheral blood mononuclear cells (PBMCs) predictably lead to suppressed T-lymphocyte activation following MSC2 co-culture, and permissive T-lymphocyte activation in co-culture with MSC1. The induction of MSCs into the pro-immune MSC1 phenotype by TLT4 activation or into the anti-inflammatory MSC2 phenotype by TLR3 activation ensures uniform and defined cells that solves an industry hurdle by providing defined and predictable cells for use in cell-based therapy applications.

Erythropoietin, also known as EPO, is a glycoprotein hormone that controls erythropoiesis, or red blood cell production. It is a cytokine or cell-signaling molecule for erythrocyte (red blood cell) precursors in the bone marrow. Human EPO has a molecular weight of 34 kDa and is also called hematopoietin or hemopoietin. EPO is produced by interstitial fibroblasts in the kidney in close association with peritubular capillary and tubular epithelial tubule and in perisinusoidal cells in the liver. While liver production predominates early in development (fetal and perinatal period), the kidney is the predominant EPO production site in adults. In addition to erythropoiesis, erythropoietin also has other known biological functions. For example, it plays an important role in the brain's response to neuronal injury by providing a pro-survival anti-apoptosis (programmed cell death) signal. EPO is also involved in the wound healing process. Synthetic erythropoietin is also produced by recombinant DNA technology in cell culture. Additionally, several different pharmaceutical EPO-like agents are available with a variety of glycosylation patterns, and are collectively called erythropoiesis-stimulating agents (ESA). EPO is used in this invention as a means to prevent premature cell death and prolong survival of the yielded primed, activated, or induced cells used in cell-based therapy.

Consistent oxygen supply is an important factor influencing all major aspects of cell biology including survival, proliferation, differentiation, and migration. Typically, mammalian cells (not stem cells) require a consistent supply of oxygen to maintain a robust energy production, and to preserve normal cell function and cell survival. By contrast, mammalian stem cells seem to thrive and persist in the hypoxic environment (with oxygen tension ranging from 0.5% to 7%) of the bone marrow. Several studies have shown that the hypoxic environment is required for maintaining the proliferation and self-renewal capability of the stem cells in the bone marrow. Particularly, the effects of reduced oxygen tension even after short-term culture of MSCs has been described as a general method of improving their engraftment capability in cell-based therapies. A hypoxic environment is used in this invention as a means to maintain the self-renewal and proliferative potential of the yielded primed, activated, or induced cells used in cell-based therapy.

DEFINITIONS & PREFERRED VALUES

For clear understanding, terms are defined and preferred values are stated here, and also throughout the text where necessary.

The term "stem cell" means a cell which is capable of giving rise to multiple different types of cells. The term "mesenchymal stem cell" or "MSC" means a stem cell originally derived from the mesenchyme. The term refers to a cell which is capable of differentiating into at least two or more of an osteoblast, a chondrocyte, an adipocyte, or a myocyte. MSCs may be isolated from any type of adult tissue. Typically MSCs are isolated from bone marrow, adipose tissue, umbilical cord, or peripheral blood. In a preferred aspect of the invention, MSCs are obtained from bone marrow or lipoaspirates, themselves obtained from adipose tissue.

The term "multipotent" and alternative term "pluripotent" mean a cell which is capable of giving rise to multiple types of cells of different tissue lineages.

The term "cellular therapy" or "cell-based therapy" means the transplantation of human or animal cells to prevent, treat, or ameliorate one or more symptoms associated with a disease or disorder, such as, but not limited to, the replacement or repair of damaged tissues or organs, the modulation of immune reactions and the reduction of inflammatory symptoms and cancers.

The term "subject" refers to an animal, preferably a mammal including non-primates (e.g., a cow, pig, horse, cat, dog, rat, or mouse) or a primate (e.g., a monkey, or a human). In a preferred embodiment, the subject is a human.

The terms "treat", "treatment", and "treating" when used directly in reference to a patient or subject mean the amelioration of one or more symptoms associated with a disorder including, but not limited to, an inflammatory disorder, an autoimmune disease or an immunologically mediated disease including rejection of transplanted organs and tissues, where the amelioration results from the administration of the immunomodulatory cells yielded by the invention, or a pharmaceutical composition comprising immunomodulatory cells yielded by the invention, to a subject in need of such treatment.

The terms "repair" and "repairing" when used directly in reference to damaged tissues means the amelioration of such damage by both direct mechanisms such as the regeneration of damaged tissues, as well as through indirect mechanisms, e.g., reducing inflammation thereby enabling tissue formation.

"Allogenic" means from different individuals of the same species. When individuals possess genes that differ at one or more loci, they are said to be allogenic. In contrast, "autologous" means from the same individual.

The term "immune disease" refers to a condition in a subject characterized by cellular, tissue and/or organ injury caused by an immunological reaction of the subject.

The term "autoimmune disease" refers to a condition in a subject characterized by cellular, tissue and/or organ injury caused by an immunological reaction of the subject to its own cells, tissues, and/or organs. Illustrative, non-limiting examples of autoimmune diseases which can be treated with the immunomodulatory cells yielded by the invention include alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CF1DS), chronic inflammatory demyelinating polyneuropathy, Churg-Strauss syndrome, cicatrical pemphigoid, CREST syndrome, cold agglutinin disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, Meniere's disease, mixed connective tissue disease, multiple sclerosis, type 1 or immune-mediated diabetes mellitus, myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, sarcoidosis, scleroderma, progressive systemic sclerosis, Sjogren's syndrome, Good pasture's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, Wegener's granulomatosis, Anti-Glomerular Basement Membrane Disease, Antiphospholipid Syndrome, Autoimmune Diseases of the Nervous System, Familial Mediterranean Fever, Lambert-Eaton Myasthenic Syndrome, Sympathetic Ophthalmia, Polyendocrinopathies, Psoriasis, etc.

"Immune disorders" include autoimmune diseases and immunologically mediated diseases.

"Immune mediated inflammatory disease" means any disease characterized by chronic or acute inflammation, resulting from, associated with, or triggered by, a dysregulation of the normal immune response; e.g., Crohn's disease, type 1 diabetes mellitus, rheumatoid arthritis, inflammatory bowel disease, psoriasis, psoriatic arthritis, ankylosing spondylitis, systemic lupus erythematosus, Hashimoto's disease, graft-versus-host disease, Sjogren's syndrome, pernicious anemia, Addison disease, scleroderma, Goodpasture's syndrome, ulcerative colitis, autoimmune hemolytic anemia, sterility, myasthenia gravis, multiple sclerosis, Basedow's disease, thrombopenia purpura, Guillain-Barre syndrome, allergy, asthma, atopic disease, arteriosclerosis, myocarditis, cardiomyopathy, glomerular nephritis, hypoplastic anemia, and rejection after organ transplantation.

The term "immunomodulatory" refers to the modification, amplification, inhibition or reduction of one or more biological activities of the immune system which includes, but is not limited to, downregulation of immune response, augmentation of immune responses and changes of the inflammatory states mediated by changes in cytokine profile, cytotoxic activity and antibody production and their effects on immune and immune related cells.

The term "inflammatory disorders" refers to a condition in a subject characterized by inflammation, e.g., chronic inflammation. Illustrative, non-limiting examples of inflammatory disorders include, but are not limited to, Celiac Disease, rheumatoid arthritis (RA), Inflammatory Bowel Disease (IBD), asthma, encephalitis, chronic obstructive pulmonary disease (COPD), inflammatory osteolysis, allergic disorders, septic shock, pulmonary fibrosis (e.g., idiopathic pulmonary fibrosis), inflammatory vacultides (e.g., polyarteritis nodosa, Wegner's granulomatosis, Takayasu's arteritis, temporal arteritis, and lymphomatoid granulomatosus), post-traumatic vascular angioplasty (e.g., restenosis after angioplasty), undifferentiated spondyloarthropathy, undifferentiated arthropathy, arthritis, inflammatory osteolysis, chronic hepatitis, and chronic inflammation resulting from chronic viral or bacteria infections.

"Isolated cell population" means a cell population, isolated from the human or animal body, which is substantially free of one or more other cell populations that are normally associated with the cell population in vivo or in vitro.

The term "ligand inducer" means an agent or agents that result in increased production of such a ligand. A ligand inducer for a Toll-like receptor (TLR) ligand will yield increased TLR ligand, and is therefore essentially equivalent to the TLR ligand itself.

The term "MHC" (major histocompatibility complex) refers to a subset of genes that encode cell-surface antigen-presenting proteins. In humans, these genes are referred to as human leukocyte antigen (HLA) genes. The abbreviations MEW or HLA are used interchangeably.

The term "population of cells" means any number of cells greater than 1, but is preferably at least $1 \times 10^3$ cells, at least $1 \times 10^4$ cells, at least $1 \times 10^5$ cells, at least $1 \times 10^6$ 6 cells, at least $1 \times 10^7$ cells, at least $1 \times 10^8$ cells, or at least $1 \times 10^9$ cells.

In preferred embodiments of this invention, at least 50%, at least 55%, at least 60%, at least 65%, at least 70%, at least 75%, at least 80%, at least 85%, at least 90%, at least 91%, at least 92%, at least 93%, at least 94% or at least 95%, of the stem cells (% by cell number) in an initial cell population will be undifferentiated MSCs.

The term "significant expression" or its equivalent terms "positive" and "+" when used regarding a cell surface marker means that, in a cell population, more than 20%, preferably more than 30%, 40%, 50%, 60%, 70%, 80%, 90% 95%, 98%, 99%, or even 100% of the cells express the cell surface marker.

Expression of cell surface markers may be determined, for example, by means of flow cytometry for a specific cell surface marker using conventional methods and apparatus (for example a BECKMAN COULTER EPICS XL FACS system used with commercially available antibodies and standard protocols known in the art) that show a signal for a specific cell surface marker in flow cytometry above the background signal using conventional methods and apparatus. The background signal is defined as the signal intensity given by a non-specific antibody of the same isotype as the specific antibody used to detect each surface marker in conventional FACS analysis. For a marker to be considered positive the specific signal observed is stronger than 20%, preferably stronger than, 30%, 40%, 50%, 60%, 70%, 80%, 90%, 500%, 1000%, 5000%, 10000% or above, than the background signal intensity using conventional methods and apparatus. Furthermore, commercially available and known monoclonal antibodies against said cell-surface markers (e.g., cellular receptors and transmembrane proteins) can be used to identify relevant cells.

DISCLOSURE OF THE INVENTION

Practice of the invention employs—except for the invention itself—conventional techniques of cell culture, molecular biology, and microbiology, which are within the skill of those working in the art.

The invention provides an inducing, activating, or priming culture induction medium for a population of multipotent stem cells (MSCs), comprising a Toll-like receptor (TLR) ligand or TLR-ligand inducer in combination with erythropoietin (EPO) and with exposure to hypoxia (preferably 0.5-2% oxygen) or hypoxia mimetic (preferably cobalt chloride or desferrioxamine), plus additional, standard components of cell-culture media known in the art and described here.

The invention also provides a culture-medium induction supplement comprising a Toll-like receptor (TLR) ligand or TLR-ligand inducer in combination with erythropoietin (EPO) and with exposure to hypoxia or hypoxia mimetic, which can be added to other, existing culture media. Such a supplement might be appropriate where unusual components or concentrations of other components are appropriate for certain circumstances.

The invention also provides a hermetically-sealed culture vessel containing the culture induction medium or culture-medium induction supplement of the invention.

The invention also provides a method for preparing a culture induction medium as disclosed herein, comprising the steps of: (a) obtaining a culture medium; and (b) adding a Toll-like receptor (TLR) ligand or TLR-ligand inducer in combination with erythropoietin (EPO) and with exposure to hypoxia (0.5-2% oxygen) or hypoxia mimetic (cobalt chloride or desferrioxamine) to the culture medium.

The invention also provides a composition comprising: (a) a culture medium according to the invention; and (b) stem cells.

The invention also provides a composition containing: (a) a culture medium according to the invention; and (b) a solid surface.

The invention also provides the use of a culture medium of the invention for inducing, activating or priming a population of multipotent stem cells.

The invention also provides an ex-vivo method for inducing, activating or priming a population of multipotent stem cells, comprising: (a) providing a population of multipotent stem cells; (b) providing a culture medium of the invention; (c) contacting the stem cells with the culture medium; and (d) culturing the cells under appropriate conditions.

In one aspect the invention provides the use of a Toll-like receptor (TLR) ligand or TLR-ligand inducer in combination with erythropoietin and with exposure to hypoxia (0.5-2% oxygen) or hypoxia mimetic (cobalt chloride or desferrioxamine) in the manufacture of a cellular therapy medicament. Accordingly in one embodiment the invention also provides a method of manufacture of a cellular therapy medicament, comprising: (a) providing a population of multipotent stem cells; (b) providing a culture medium of the invention; (c) contacting the stem cells with the culture medium; and (d) culturing the cells under appropriate conditions. The invention also provides the use of a composition comprising: (a) a culture medium according to the invention; and (b) stem cells, for manufacturing a cellular therapy medicament. The invention also provides the use of a composition comprising: (a) a culture medium according to the invention; and (b) a solid surface, for manufacturing a cellular therapy medicament.

Said medicaments are of use in the treatment, repair, prophylaxis, and/or amelioration of damaged tissues, or one or more symptoms associated with inflammatory and/or immune disorders such as but not limited to autoimmune diseases, inflammatory disorders, and immunologically mediated diseases including rejection of transplanted organs and tissues and cancer. A cellular therapy medicament of the invention comprises a prophylactically or therapeutically effective amount of stem cells and a pharmaceutical carrier. Particularly preferred are stem cells of mesenchymal origin, most preferably bone marrow-derived stem cells. Examples of dosages and dosage regimens for each of these cell types are known in the art. Suitable pharmaceutical carriers are known in the art and are preferably those approved by a regulatory agency of the US Federal or a state government or listed in the U S Pharmacopeia, or European Pharmacopeia, or other generally recognized pharmacopeia for use in animals, and more particularly in humans. The term "carrier" refers to a diluent, adjuvant, excipient, or vehicle with which the therapeutic agent is administered. The composition, if desired, can also contain minor amounts of pH buffering agents. Examples of suitable pharmaceutical carriers are described in "Remington's Pharmaceutical Sciences" by E W Martin. Such compositions will contain a prophylactically or therapeutically effective amount of a prophylactic or therapeutic agent preferably in purified form, together with a suitable amount of carrier so as to provide the form for proper administration to the subject. The formulation should suit the mode of administration. In a preferred embodiment, the medicaments are sterile and in suitable form for administration to a subject, preferably an animal subject, more preferably a mammalian subject, and most preferably a human subject.

The medicament of the invention may be in a variety of forms. These include, for example, semi-solid, and liquid dosage forms, such as lyophilized preparations, liquid solutions or suspensions, injectable and infusible solutions, etc., the medicament is preferably injectable.

It is preferred that the medicaments are for treating or repairing damaged tissue (preferably mesenchymal tissue), and/or for the treatment, modulation, prophylaxis, and/or amelioration of one or more symptoms associated with inflammatory and/or immune disorders. Accordingly the methods and cells of the invention are of use in the treatment of any disorder characterized by either or all of said symptoms. A representative non-exhaustive list of such disorders is provided in the definitions section. Particularly preferred is a medicament for the treatment of immune-mediated inflammatory diseases. Further preferred is a medicament for the treatment of diabetes mellitus, rheumatoid arthritis (RA), inflammatory bowel disease (IBD, including Crohn's disease and/or Ulcerative Colitis) and multiple sclerosis (MS). The invention also provides the use of a Toll-like receptor (TLR) ligand or TLR-ligand inducer in combination with erythropoietin and with exposure to hypoxia (0.5-2% oxygen) or hypoxia mimetic (cobalt chloride or desferrioxamine) for multipotent stem cell culture.

The specific ingredients and ratio of ingredients of the culture media, supplements and compositions of the invention can vary according to particular needs and applications. Likewise, the precise steps of the methods of the invention can vary according to particular needs and applications. The culture media, supplements, methods, compositions and uses according to this invention may be optimised by routine experimentation. For example, if a desired outcome is an anti-inflammatory therapeutic effect, if a culture medium, supplement or composition will specifically contain a TLR3 ligand or TLR-ligand inducer in combination with erythropoietin and with exposure to hypoxia (0.5-2% oxygen) or hypoxia mimetic (cobalt chloride or desferrioxamine) by contrast, if a desired outcome is a pro-immune therapeutic effect, if a culture medium, supplement or composition will specifically contain a TLT4 ligand or TLR-ligand inducer in combination with erythropoietin and with exposure to hypoxia (0.52% oxygen) or hypoxia mimetic (cobalt chloride or desferrioxamine). The amount of each of the ingredients described herein can be optimised independently of the other ingredients by routine optimisation or one or more ingredients can be added or removed. A culture medium can be tested for its ability to support induction, activation or priming of multipotent stem cells by testing it alongside or in place of a known culture medium or method. The culture media, supplements, methods, compositions and uses of the invention are described in more detail below.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

The induction media of the invention comprises a Toll-like receptor (TLR) ligand or TLR-ligand inducer in combination with erythropoietin and with exposure to hypoxia (0.5-2% oxygen) or hypoxia mimetic (cobalt chloride or desferrioxamine). In one aspect the induction media of the invention comprises a Toll-like receptor (TLR) ligand or TLR-ligand inducer. In an alternative aspect the induction media of the invention comprises erythropoietin and exposure to hypoxia (0.5-2% oxygen) or hypoxia mimetic (cobalt chloride or desferrioxamine). In a further aspect the induction media of the invention comprises a Toll-like receptor (TLR) ligand or TLR-ligand inducer in combination with erythropoietin and with exposure to hypoxia (0.5-2% oxygen) or hypoxia mimetic (cobalt chloride or desferrioxamine).

The induction media of the invention may comprise two or more, three or more, 4-, 5-, 6-, 7-, 8-, 9-, 10- or more, combinations of a Toll-like receptor (TLR) ligand or TLR-ligand inducer in combination with erythropoietin (EPO) and with exposure to hypoxia (0.5-2% oxygen) or hypoxia mimetic (cobalt chloride or desferrioxamine).

An induction medium of the invention may comprise between about 0.10 picomolar (pM) and about 100 millimolar (mM) of a TLR ligand or TLR-ligand inducer in combination with about 0.5 mU/mL and about 50 mU/mL erythropoietin (EPO) and with exposure to about 0.5 to about 2% oxygen conditions (hypoxia) or hypoxia mimetic such as cobalt chloride or desferrioxamine, at a concentration of about 10 micromolar to about 1 mM, or any other combination of the above TLR ligand or TLR-ligand inducer, erythropoietin, and hypoxia.

Cell induction media typically contain a large number of ingredients, which are necessary to support maintenance of the cultured cells. An induction medium of the invention will therefore normally contain many other ingredients in addition to a Toll-like receptor (TLR) ligand or TLR-ligand inducer in combination with erythropoietin and with exposure to hypoxia (0.5-2% oxygen) or hypoxia mimetic (cobalt chloride or desferrioxamine). Suitable combinations of ingredients can readily be formulated by the skilled person, taking into account the following disclosure. An induction medium according to the invention will generally be a nutrient solution comprising standard cell culture ingredients, such as amino acids, vitamins, trace metals, inorganic salts, a carbon energy source, and a buffer, as described in more detail below.

An induction medium of the invention may contain serum. Serum contains cellular and non-cellular factors and components that may be necessary for viability and expansion. Serum obtained from any appropriate source may be used, including fetal bovine serum (FBS), bovine serum (BS), calf serum (CS), fetal calf serum (FCS), newborn calf serum (NCS), goat serum (GS), horse serum (HS), porcine serum, sheep serum, rabbit serum, rat serum (RS), etc. It is also within the scope of the invention that if said MSC are of human origin, the cell induction medium is supplemented with a human serum, preferably of autologous origin. It is understood that sera can be heat inactivated at 55-65 deg. C. if deemed necessary to inactivate components of the complement cascade. Where a serum replacement is used, it may be used at between about 2% and about 40% by volume of the medium, according to conventional techniques.

In other embodiments, an induction medium of the invention may contain a serum replacement. Various different serum replacement formulations are commercially available and are known to the skilled person, such as but not limited to serum albumin, serum transferrin, selenium, and recombinant proteins including but not limited to insulin, platelet-derived growth factor (PDGF), and basic fibroblast growth factor (bFGF). Where a serum replacement is used, it may be used at between about 2% and about 40% by volume of the medium, according to conventional techniques. In other embodiments, an induction medium of the invention may be serum-free and/or serum replacement-free. A serum-free medium is one that contains no animal serum of any type. Serum-free media may be preferred to avoid possible xeno-contamination of the stem cells. A serum replacement-free medium is one that has not been supplemented with any commercial serum replacement formulation.

An induction medium of the invention will normally be formulated in deionized, distilled water. An induction medium of the invention will typically be sterilized prior to use to prevent contamination, e.g. by ultraviolet light, heating, irradiation or filtration. The induction medium may be frozen (e.g. at −20° C. or −80° C.) for storage or transport. Antimicrobial agents are also typically used in media to mitigate bacterial, mycoplasmal, and fungal contamination. The medium may contain one or more antimicrobial agents or antibiotics to prevent contamination. Typically, antibiotics or anti-mycotic compounds used are mixtures of penicillin/streptomycin, but can also include, but are not limited to amphotericin (Fungizone®), ampicilhn, gentamicin, bleomycin, hygromacin, kanamycin, mitomycin, etc.

In one embodiment of the invention, the culture medium is a medium that has been conditioned by the addition of cells induced by a Toll-like receptor (TLR) ligand or TLR-ligand inducer in combination with erythropoietin and with exposure to hypoxia (0.5-2% oxygen) or hypoxia mimetic (cobalt chloride or desferrioxamine). Conditioned medium is produced by culturing a population of said cells in a induction medium for a time sufficient to condition the medium, then harvesting the conditioned medium. Where a conditioned medium is used, the medium may be conditioned on mammalian cells, e.g. mouse cells or human cells. Various different types of mammalian cells may be used to produce conditioned medium suitable for multipotent stem cell induction.

An induction medium may be a 1× formulation or a concentrated formulation, e.g. a 2× to 250× concentrated medium formulation. In a 1× formulation each ingredient in the medium is at the concentration intended for cell induction. In a concentrated formulation one or more of the ingredients is present at a higher concentration than intended for cell induction. Induction medium can be concentrated using known methods e.g. salt precipitation or selective filtration. A concentrated medium may be diluted for use with water (preferably deionized and distilled) or any appropriate solution, e.g. an aqueous saline solution, an aqueous buffer or a culture medium.

An induction medium as disclosed herein may be capable of inducing, activating or priming a population of stem cells in a multipotent, undifferentiated and proliferative state for only a single passage or population doubling under appropriate conditions. Stem cells are considered to be in a multipotent, undifferentiated and proliferative state if they exhibit certain characteristics as described in more detail elsewhere herein. Appropriate conditions can be selected by the skilled person from those normally used for multipotent stem cell culture.

As noted elsewhere herein, the invention also provides a hermetically-sealed vessel containing an induction medium of the invention. Hermetically-sealed vessels may be preferred for transport or storage of the induction media, to prevent contamination. The vessel may be any suitable vessel, such as a bioreactor, a flask, a plate, a bottle, a jar, a vial or a bag. As noted elsewhere herein, the invention also provides a method for preparing an induction medium, comprising the steps of: (a) obtaining a culture medium; and (b) adding a Toll-like receptor (TLR) ligand or TLR-ligand inducer in combination with erythropoietin (EPO) and with exposure to hypoxia (0.5-2% oxygen) or hypoxia mimetic (cobalt chloride or desferrioxamine) to the culture medium. Various different methods for preparing induction media are envisaged, depending on the specific ingredients to be included in the induction medium. For example, a method for preparing a induction medium may comprise the steps of: (a) obtaining a culture medium; and (b) adding a TLR ligand or TLR-ligand inducer in combination with erythropoietin (EPO) and with exposure to hypoxia (0.5-2% oxygen) or hypoxia mimetic (cobalt chloride or desferrioxamine) to the culture medium. In one embodiment, a method for preparing an induction medium may comprise the steps of: (a) obtaining a culture medium; and (b) adding a TLR ligand, EPO and cobalt chloride to the culture medium.

The induction media of the invention can be used to induce, activate or prime a population of multipotent stem cells. Accordingly, the invention provides the use of any induction medium as disclosed herein for inducing, activating or priming a population of multipotent stem cells into discrete uniform phenotypes for cell-based therapy.

The invention also provides an ex-vivo method for inducing, activating or priming a population of multipotent stem cells, comprising: (a) providing a population of multipotent stem cells; (b) providing a induction medium as disclosed herein; (c) contacting the stem cells with the induction medium; and (d) culturing the stem cells under appropriate conditions.

The invention also provides a method cellular therapy, comprising: (a) providing a population of multipotent stem cells; (b) providing an induction medium of the invention; (c) contacting the stem cell population with the induction medium; and (d) culturing the cells under appropriate conditions.

The methods of the invention may comprise culturing the cells in contact with a solid surface as described elsewhere herein. For example, the invention provides a method comprising: (a) providing a population of multipotent stem cells;

(b) providing an induction medium as disclosed herein; (c) contacting the stem cells with the induction medium; and (d) culturing the cells under appropriate conditions and in contact with a solid surface. The invention also provides the use of an induction medium as disclosed herein and a solid surface to expand a population of multipotent stem cells. The multipotent stem cells may adhere, attach or be seeded onto said support. Typically, the cells are plated at a desired density such as between about 100 cells/cm2 to about 100,000 cells/cm2 (such as about 500 cells/cm2 to about 50,000 cells/cm2, or, more particularly, between about 1,000 cells/cm2 to about 20,000 cells/cm2) prior to inducing, activating or priming of the stem cells. In a particular embodiment, the cell density is between 200-10,000 cells/cm2.

It will be appreciated that the steps of the methods disclosed herein can be performed in any suitable order or at the same time, as appropriate, and need not be performed in the order in which they are listed. For example, in the above method the step of providing a population of multipotent stem cells may be performed before, after or at the same time as, the step of providing an induction medium.

The methods and uses of the invention may involve any induction medium or supplement as described herein. Accordingly, in some embodiments the methods of the invention may be serum and/or serum replacement-free methods. In some embodiments, the methods of the invention may be used to induce cells in the absence of contact with a layer of feeder cells.

The preferred methods and uses of the invention are for the inducing, activating or priming of the population of multipotent stem cells to occur once the cells have been expanded and prior to being cryopreserved and used in cell-based therapy.

It is preferred that said stem cell population is of adult origin, and it is further preferred that said cells are a mesenchymal stem cell population, as in bone marrow-derived or adipose tissue-derived cells.

Conditions for the culture of stem cells are known to the person skilled in the art. It is preferred that the culture is carried out in the presence of a solid support suitable for the adherence of mesenchymal stem cells.

Said method of manufacture may optionally further comprise the steps of: (a) passaging the cells into a culture medium as disclosed herein; (b) further culturing the cells under appropriate conditions and (c) inducing, activating or priming the cells.

It has been shown that ex vivo expansion of the MSC without inducing differentiation can be accomplished for extended time periods for example by using specially screened lots of suitable serum (such as fetal bovine serum or human serum). Methods for measuring viability and yield are known in the art (e.g., trypan blue exclusion).

Any of the steps and procedures for isolating the cells of the cell population of the invention can be performed manually, if desired. Alternatively, the process of isolating such cells can be facilitated and/or automated through one or more suitable devices, examples of which are known in the art.

Practice of the invention may be performed using any suitable cell culture vessel as a support. Cell culture vessels of various shapes and sizes (e.g. flasks, single or multiwell plates, single or multiwell dishes, bottles, jars, vials, bags, bioreactors) and constructed from various different materials (e.g. plastic, glass) are known in the art. A suitable cell culture vessel can readily be selected by the skilled person.

The invention also provides a culture-medium induction supplement that can be used to produce a culture induction medium as disclosed here. A "culture-medium induction supplement" is a mixture of ingredients that cannot itself support multipotent stem cells, but which enables or improves multipotent stem cell culture when combined with other cell culture-medium ingredients. The supplement can therefore be used to produce a functional cell culture medium of the invention by combining it with other cell culture ingredients to produce an appropriate medium formulation. The use of culture medium supplements is well known in the art. The invention provides a culture-medium induction supplement that comprises adding a TLR ligand or TLR-ligand inducer in combination with erythropoietin (EPO) and with exposure to hypoxia (0.5-2% oxygen) or hypoxia mimetic (cobalt chloride or desferrioxamine). The supplement may contain any ligands disclosed herein. The supplement may also contain one or more additional cell culture ingredients, e.g. one or more cell culture ingredients selected from the group consisting of amino acids, vitamins, inorganic salts, trace elements, carbon energy sources and buffers.

A culture-medium induction supplement may be a concentrated liquid supplement (e.g., a 2× to 250× concentrated liquid supplement) or may be a dry supplement. Both liquid and dry types of supplements are well known in the art. A supplement may be lyophilized.

A culture-medium induction supplement of the invention will typically be sterilized prior to use to prevent contamination, e.g., by ultraviolet light, heating, irradiation or filtration. A culture-medium induction supplement may be frozen (e.g. at −20° C. or −80° C.) for storage or transport.

The invention also provides a hermetically-sealed vessel containing a culture medium supplement of the invention. Hermetically-sealed vessels may be preferred for transport or storage of the culture media supplements disclosed herein, to prevent contamination. The vessel may be any suitable vessel, such as a bioreactor, a flask, a plate, a bottle, a jar, a vial, or a bag.

A variety of substances have been used as surfaces for adherent stem cell culture, and an appropriate material can readily be selected by the skilled person. Preferably, the solid surface comprises plastic but may alternatively comprise of glass, extracellular matrix. The surface may be planar, tubular, or in the form of a scaffold, bead or fibre.

The compositions of the invention may comprise serum, or may be serum-free and/or serum-replacement free, as described elsewhere herein.

'Multipotent' stem cells are those that have the potential to differentiate into cells of all three germ layers (endoderm, mesoderm and ectoderm) under appropriate conditions. Multipotent stem cells are not totipotent, i.e. they cannot form an entire organism, such as a foetus. Multipotent stem cells for use in the invention can be obtained using well-known methods (see below). It is envisaged that various types of multipotent stem cells may be used in conjunction with the invention, whether obtained from embryonic, foetal, or adult tissue but are preferably derived from adult tissue sources.

The induction media disclosed herein may be used to culture mammalian stem cells, particularly human adult stem cells. Human adult stem cells that may be used in conjunction with the invention are preferably mesenchymal stem cells. Mouse or primate stem cells may also be used. In preferred embodiments, the stem cells are human bone marrow-derived stem cells (MSC).

Multipotent stem cells may be identified by their ability to differentiate into cells of all three germ layers e.g. by determining the ability of the cells to differentiate into cells showing detectable expression of markers specific for all three germ layers. References in the singular (e.g. to "a cell" and equivalent references) encompass the plural (e.g. "cells") unless the context requires otherwise.

The induction media of the invention can be used to induce, activate or prime a population of multipotent stem cells. Accordingly, the invention provides the use of any induction medium as disclosed herein for inducing, activating or priming a population of multipotent stem cells into discrete uniform phenotypes for cell-based therapy. These discrete and uniform phenotypes can be an anti-inflammatory MSC phenotype (MSC2), and a uniform and discrete pro-immune anti-tumor MSC phenotype (MSC1).

The preferred method of induction for a uniform and discrete anti-inflammatory MSC phenotype (MSC2) is incubation of the MSC with a culture medium containing a Toll-like receptor-3 (TLR3) ligand such as polyinosinic:polycytidylic acid (or poly(I:C); 1 μg/mL) in combination with erythropoietin (1 mU/mL or 5 ng/mL) and with exposure to hypoxia (1% oxygen) or hypoxia mimetic (cobalt chloride or desferrioxamine, either at 200 μM) for 1 hour upon 70-90% confluent growth.

The preferred method of induction for a uniform and discrete pro-immune anti-tumor MSC phenotype (MSC1) is incubation of the MSC with a culture medium containing a Toll-like receptor-4 (TLR4) ligand such as lipopolysaccharide (LPS, endotoxin at 10 ng/mL) in combination with erythropoietin (1 mU/mL or 5 ng/mL) and with exposure to hypoxia (1% oxygen) or hypoxia mimetic (cobalt chloride or desferrioxamine, either at 200 μM)) for 1 hour upon 70-90% confluent growth.

TLR-ligands in combination with erythropoietin and with exposure to hypoxia (0.5-2% oxygen) or hypoxia mimetic (cobalt chloride or desferrioxamine) are added to fresh culture medium, or as a culture supplement and incubated with the cells for 1 hr. Following this induction step, the MSC are washed twice in culture medium or suitable buffered saline solution without the TLR-ligands to remove cell and culture debris. Without wishing to be bound by theory, short incubation times (<1 hr) and minimal TLR ligand exposure at the concentrations noted above (or lower) are important for achieving the desired phenotypes and, further, this protocol mimics the gradient of danger signals that endogenous MSCs encounter and respond to at a distance from the site of injury. Once washed, the induced, activated, or primed MSC can be harvested by traditional methods e.g.—trypsin and EDTA for between 5 seconds and 15 minutes at 37° C. or with a trypsin substitute (e.g. TrypLE from Invitrogen), collagenase, dispase, accutase or other reagents known to the person skilled in the art. Following cell harvest the primed, activated, or induced MSC can be cryopreserved by standard methods.

The TLR3 ligand used in the induction culture medium may be IL4, IL13, poly(A:U), poly(I:C), and combinations thereof, and may be delivered by incubation, transfection, transduction, by carrier molecules, or by combinations thereof. Preferably, the TLR3 ligand or agonist is poly(I: C).

The TLT4 ligand used in the induction culture medium may be aminoalkyl glucosaminide 4-phosphates, interferons, TNF-alpha, GM-CSF, lipopolysaccharide (LPS), and combinations thereof, and may be delivered by incubation, transfection, transduction, by carrier molecules, or by combinations thereof. Preferably, the TLT4 ligand or agonist is LPS.

The TLR3 agonist or TLT4 agonists may be delivered by incubation, transfection, transduction by carrier molecules, or by other techniques known to those of ordinary skill in the art.

The TLR3 ligand or agonist may be provided in an amount from about 10 pg/mL to about 100 μg/mL, from about 100 pg/mL to about 100 μg/mL, from about 1 ng/mL to about 100 μg/mL, from about 5 ng/mL to about 100 μg/mL, from about 10 ng/mL to about 100 μg/mL, from about 100 ng/mL to about 100 μg/mL, from about 0.1 μg/mL to about 50 μg/mL, from about 0.1 μg/mL to about 10 μg/mL, from about 0.25 μg/mL to about 7.5 μg/mL, from about 0.5 mL to about 5 μg/mL, from about 1 μg/mL to about 2.5 μg/mL, and preferably from about 1 μg/mL to about 1.5 μg/mL in culture medium or supplement as noted above.

The TLT4 ligand or agonist may be provided in an amount from about 10 pg/mL to about 10 μg/mL, from about 100 pg/mL to about 10 μg/mL, from about 1 ng/mL to about 1 μg/mL, from about 5 ng/mL to about 1 μg/mL, from about 10 ng/mL to about 1 μg/mL, from about 100 ng/mL to about 1 μg/mL, preferably from about 5 ng/mL to about 50 ng/mL, and also preferably from about 5 ng/mL to about 25 ng/mL in culture medium or supplement as noted above.

The cells may be incubated with TLR ligand or agonist ligand in combination with erythropoietin (EPO) and with exposure to hypoxia (0.5-2% oxygen) or hypoxia mimetic (cobalt chloride or desferrioxamine) for from about 1 minute to about 480 minutes, from about 5 minutes to about 475 minutes, from about 10 minutes to about 470 minutes, from about 15 minutes to about 400 minutes, from about 20 minutes to about 120 minutes, from about 25 minutes to about 90 minutes, from about 30 minutes to about 80 minutes, from about 35 minutes to about 70 minutes, from about 40 minutes to about 65 minutes, from about 45 minutes to about 60 minutes, from about 55 minutes to about 60 minutes, and preferably about 60 minutes.

While this invention has been described in detail with particular reference to its preferred embodiments, the principles and modes of operation of the invention have also been described in this specification. The invention should not be construed as being limited to the particular forms disclosed, which are illustrative rather than restrictive. Modifications, variations, and changes may be made by those skilled in the art without departure from the spirit and scope of the invention as described by the following claims.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:
1. A cell culture comprising:
  (a) multipotent stem cells; and
  (b) culture medium comprising:
    (i) a Toll-like receptor-4 ligand (TLR4 ligand) at a concentration from about 100 pg/ml to about 10 μg/ml, and
    (ii) erythropoietin;
  wherein the cell culture is present in a hypoxic environment.

2. The cell culture of claim 1, wherein the multipotent stem cells are mesenchymal stem cells.

3. The cell culture of claim 1, wherein the TLR4 ligand is lipopolysaccharide (LPS).

4. The cell culture of claim 1, wherein the TLR4 ligand is an aminoalkyl glucosaminide-4-phosphate.

5. The cell culture of claim 1, wherein the culture medium further comprises one or more of an interferon, tumor necrosis factor alpha (TNF-α) or granulocyte-macrophage colony-stimulating factor (GM-CSF).

6. The cell culture of claim 1, wherein the hypoxic environment is generated by the presence of a hypoxia mimetic in the culture medium.

7. The cell culture of claim 6, wherein the hypoxia mimetic is cobalt chloride or desferrioxamine.

8. The cell culture of claim 1, wherein the hypoxic environment is 0.5-2.0% oxygen.

9. The cell culture of claim 1, wherein the medium is serum-free.

10. The cell culture of claim 1, wherein the multipotent stem cells are human cells.

11. The cell culture of claim 1, wherein the multipotent stem cells are mouse or primate stem cells.

12. The cell culture of claim 1, wherein the multipotent stem cells are of adult origin.

13. The cell culture of claim 1, wherein the culture is produced by culturing the multipotent stem cells in the culture medium for about one minute to about 480 minutes.

14. The cell culture of claim 1, wherein:
  (a) the TLR4 ligand is lipopolysaccharide at a concentration of 10 ng/ml;
  (b) erythropoietin is present at a concentration of 1 mU/ml or 5 ng/ml; and
  (c) either cobalt chloride or desferrioxamine is present at a concentration of 200 μM;
  and, wherein the culture is produced by culturing the multipotent stem cells in the culture medium for about one hour or less.

* * * * *